US011224490B2

(12) United States Patent
MacMillan et al.

(10) Patent No.: US 11,224,490 B2
(45) Date of Patent: Jan. 18, 2022

(54) METHOD FOR PERFORMING SPINAL SURGICAL PROCEDURES THROUGH THE SACRAL ALA

(71) Applicants: Michael MacMillan, St Petersburg, FL (US); Raymond Cloutier, Alachua, FL (US)

(72) Inventors: Michael MacMillan, St Petersburg, FL (US); Raymond Cloutier, Alachua, FL (US)

(*) Notice: Subject to any disclaimer, the term of this patent is extended or adjusted under 35 U.S.C. 154(b) by 0 days.

(21) Appl. No.: 17/033,671

(22) Filed: Sep. 25, 2020

(65) Prior Publication Data
US 2021/0346064 A1    Nov. 11, 2021

Related U.S. Application Data

(60) Provisional application No. 62/905,676, filed on Sep. 25, 2019, provisional application No. 62/905,580, filed on Sep. 25, 2019.

(51) Int. Cl.
*A61B 17/70* (2006.01)
*A61B 34/30* (2016.01)

(52) U.S. Cl.
CPC .......... *A61B 34/30* (2016.02); *A61B 17/7055* (2013.01); *A61B 17/7082* (2013.01)

(58) Field of Classification Search
CPC ............................ A61B 17/7055; A61B 34/30
See application file for complete search history.

(56) References Cited

U.S. PATENT DOCUMENTS

| | | | | | |
|---|---|---|---|---|---|
| 4,979,949 | A | * | 12/1990 | Matsen, III | A61B 17/15 606/53 |
| 5,242,444 | A | * | 9/1993 | MacMillan | A61B 17/1757 606/60 |
| 5,584,831 | A | * | 12/1996 | McKay | A61B 17/7005 606/260 |
| 2006/0235414 | A1 | * | 10/2006 | Lim | A61F 2/4425 623/17.14 |

OTHER PUBLICATIONS

MacMillan, Michael. "'Very' Future Directions in Minimally Invasive Spinal Surgery.' The Spine E-Book: Expert Consult, 2011, vol. 1, Chapter 61.*

* cited by examiner

*Primary Examiner* — Christian A Sevilla
(74) *Attorney, Agent, or Firm* — Maxwell L. Minch; Maxwell L Minch Esq. PA (57) ABSTRACT

The present invention provides for improved surgical methods for securely fix the L5 vertebrae to the S1 sacrum within the disc space for patients exhibiting a wide range of anatomies. The present invention has at least one advantage of providing practical and advantageous methods for accessing the spinal vertebrae to insert spinal implants in various manners that overcome the disadvantages of posterior, trans-sacro-iliac and anterior lateral approaches thereto and minimize surgical trauma to the patient. Thus the present invention provides for the unmet need for an improved method for performing spinal surgical procedures (e.g., spinal fusion and/or fixations) that can securely fix the L5 vertebrae to the S1 sacrum within the disc space for patients exhibiting a wide range of anatomies.

16 Claims, 11 Drawing Sheets

METHOD FOR PERFORMING SPINAL SURGICAL PROCEDURES THROUGH THE SACRAL ALA

CROSS-REFERENCE TO RELATED APPLICATIONS

This application claims the benefit of U.S. Provisional Application No. 62/905,676, having a filing date of Sep. 25, 2019, and U.S. Provisional Application No. 62/905,580 having a filing date of Sep. 25, 2019, the disclosures of which is hereby incorporated by reference in its entirety and all commonly owned.

FIELD OF THE INVENTION

The present disclosure generally relates to methods for performing spinal surgical procedures in a human. More particularly, the disclosure generally relates to methods for performing spinal surgical procedures by accessing a spinal column through the sacral ala.

BACKGROUND OF THE INVENTION

Description of the Relevant Art

Minimal invasive surgery (MIS) has several benefits over more traditional surgical techniques. Benefits include a lower rate of morbidity, reduced pain, reduced scarring, reduced blood loss and reduced recovery time and costs. In minimal invasive spine surgery, small incisions, typically about 0.5 to about 4.0 centimeters in length, are made in, for example a patient's back.

U.S. Pat. No. 5,242,444 (hereinafter "'444") discloses a method for percutaneously fixing or fusing the lumbosacral joint of a patient comprising the step of placing bone penetration instrumentation bilateral of the spine through the pedicles of S1 across the S1-L5 disk into the vertebral body of L5. However, the method that '444 discloses does not provide a means for ensuring surgical accuracy and reproducibility.

International publication WO 2000048521A1 discloses methods for percutaneously accessing the patient's intervertebral space by creating an access portal through the patient's ilium and into the patient's intervertebral space. The access portal created is preferably at a posterolateral angle, (preferably in the range of 40 to 90 degrees to an anterior/posterior axis through the patient). However, the method described requires the use of a cannula system that adds cost and complexity to the surgical procedure. Furthermore, no means is disclosed for defining and ensuring the pathway to the spine is optimally located and maintained in the desired location.

A further extension of minimally invasive surgery that is being developed currently involves using instruments that are operated and controlled by robots to access internal cavities, bones and organs within subjects. Robotic spine surgery uses conventional surgical access locations and approaches, for example, the central region of a patient's back (i.e. 'posterior approach'). Robotic spine surgery provides benefits in accuracy and reproducibility for placing spinal implants. Robotic spine surgery is often used to position a surgical instrument in accordance with a virtual image of a patient's anatomy that is generated by an MRI or CT scan. In addition to the improved accuracy and reproducibility that a robot provides, the robot has the potential to reduce the size of the surgical incision in order to provide the patient a less invasive surgery, and thus reduced trauma to the subject.

Robotic spine surgery procedures have been used to place pedicle screws using a posterior approach. U.S. Pat. No. 7,887,567 (hereinafter "'567") discloses a method of ensuring a robotically assisted spine surgery can be accomplished even if the relationship between the vertebra and the surgical robot changes intraoperatively. However, '567 does not disclose a method capable of performing a spinal fusion between the L5 vertebra and the sacrum (hereinafter "L5/S1 fusion") through the ala.

Mattei, et al. "Current state-of-the-art and future perspectives of robotic technology in neurosurgery. Neurosurgical review. 2014" (hereinafter "Mattei") discloses a review and analysis of the state of the art as it relates to spinal robotic surgery. However, Mattei does not disclose a method capable of robotically preparing for or performing an L5/S1 fusion through the ala of a human.

U.S. Pat. No. 8,439,925 (hereinafter "'925") discloses a method of accessing the lumbosacral joint through an iliac ala, sacroiliac joint, and sacral ala to a region of a L5-S1 disc space. However, '925 discloses a method that requires a pathway through the sacroiliac joint. Violating the sacroiliac joint can lead to clinical complications and morbidities.

U.S. Pat. No. 8,790,406 (hereinafter "'406") discloses a method of accessing the L5/S1 disc of the lumbosacral junction through a hole in the ilium. However, '406 does not disclose a method of accessing the L5/S1 disc via the ala.

PCT WO2012036872 (hereinafter "'872") discloses a method for fusing the spine, the method comprising: forming a passage through the ala of the sacrum to access the lumbosacral disc; passing a spacer through the passage; and implanting the spacer within disc. However, the method that is '872 discloses does not provide a means for ensuring surgical accuracy and reproducibility.

U.S. Patent Application No. 62/843,613 (hereinafter "'613") discloses devices for performing L5/S1 fusion. In some embodiments, '613 discloses devices for performing L5/S1 fusion that are positioned in the ala, L5/S1 disc space and L5 vertebra. However, '613 does not disclose a method in which access to the surgical site to receive the disclosed devices is enabled.

What is needed is an improved method for performing spinal Surgical procedures (e.g., spinal fusions) using one or more ala as the pathway to the L5 vertebrae and L5/S1 disc space without violating the sacro-iliac joint.

SUMMARY OF INVENTION

The present invention provides for an improved method for performing spinal Surgical procedures (e.g., spinal fusions) using one or more ala as the pathway to the L5 vertebrae and L5/S1 disc space without violating the sacro-iliac joint. One aspect of the present invention is that it provides a surgical method to securely fix the L5 vertebrae to the S1 sacrum within the disc space for patients exhibiting a wide range of anatomies. Another aspect of the present invention is to provide practical and advantageous methods for accessing the spinal vertebrae to insert spinal implants in various manners that overcome the disadvantages of posterior, trans-sacro-iliac and anterior lateral approaches thereto and minimize surgical trauma to the patient. Yet, another aspect of the present invention provides for mechanical and robot methods and pathways to optimize spinal fusion and implant surgeries.

BRIEF DESCRIPTION OF THE DRAWINGS

Examples illustrative of embodiments of the disclosure are described below with reference to figures attached hereto. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings. The figures (Figs.) are listed below.

Figure 1:
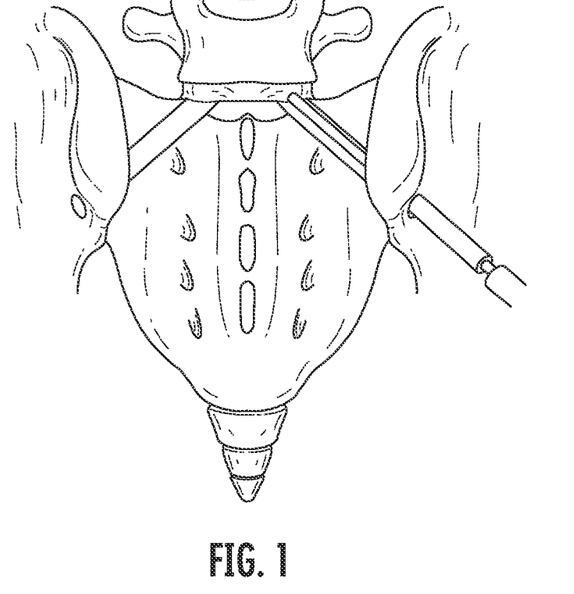
FIG. 1 provides an example of pathways formed by instruments positioned with an end-effector in the Subjects' right and left ala, L5/S1 disc and L5 vertebra.
Figure 2A:
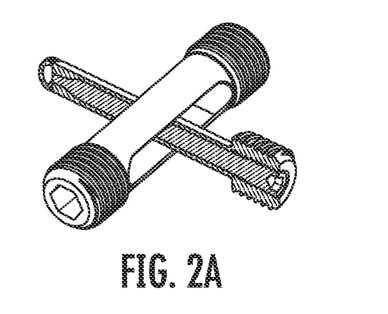
FIG. 2 provides for at least one embodiment of an implant which may be used with the inventive methods.
Figure 2B:
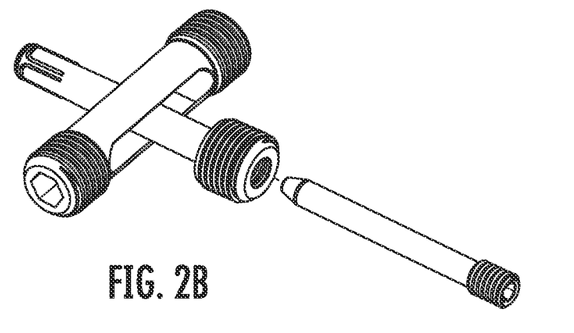
Figure 3:
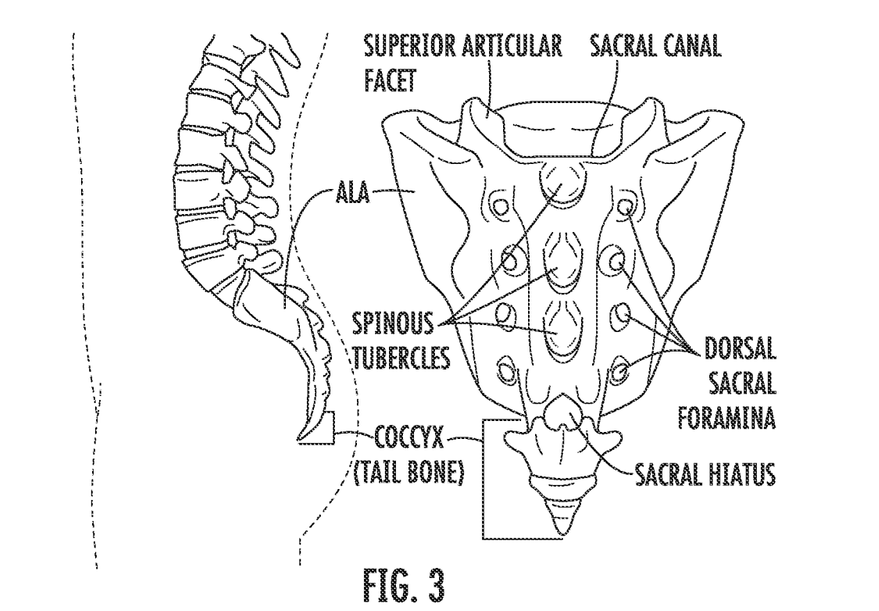
FIG. 3 describes the key anatomic structures of the sacrum.
Figure 4:
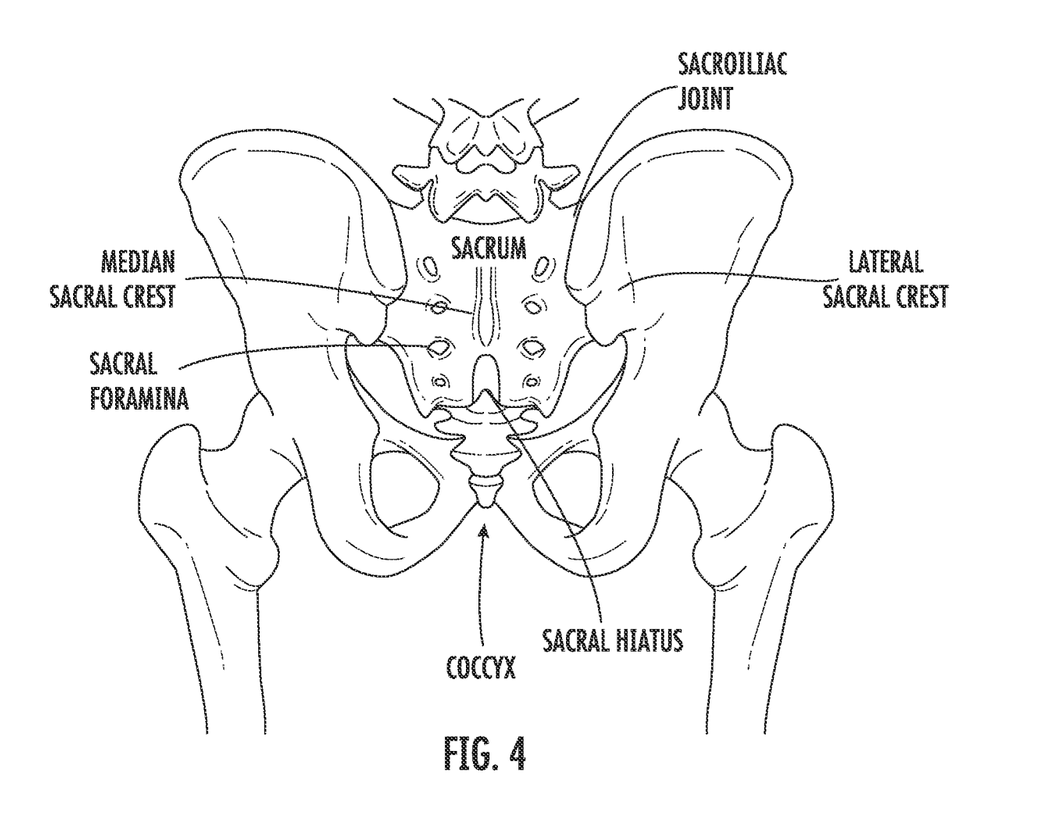
FIG. 4 describes the key anatomic structures of the sacrum and ilium.
Figure 5:
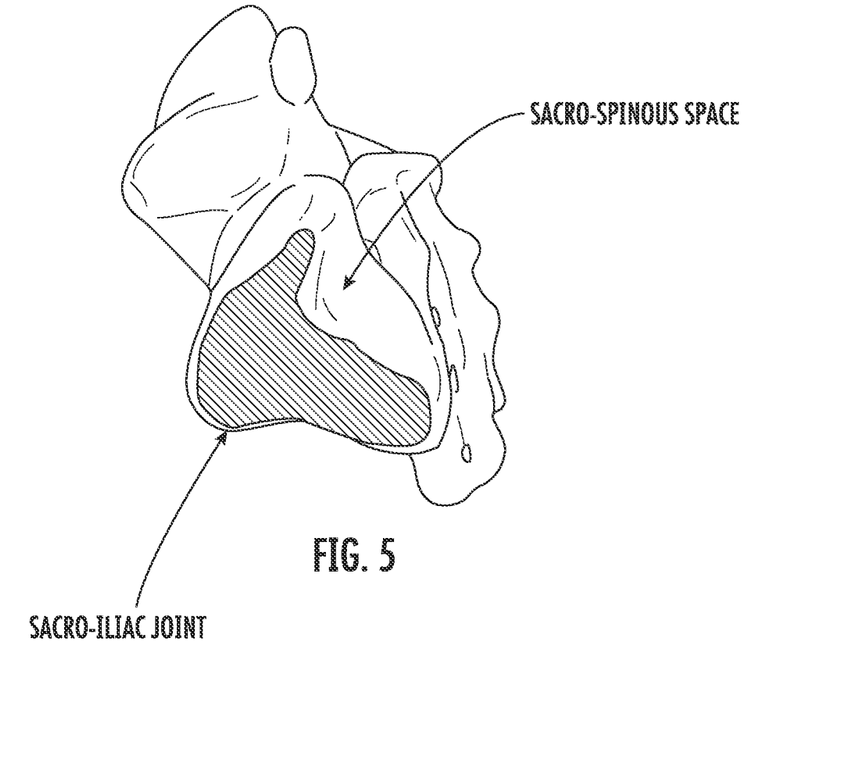
FIG. 5 describes the key anatomic structures of the sacrum.
Figure 6:
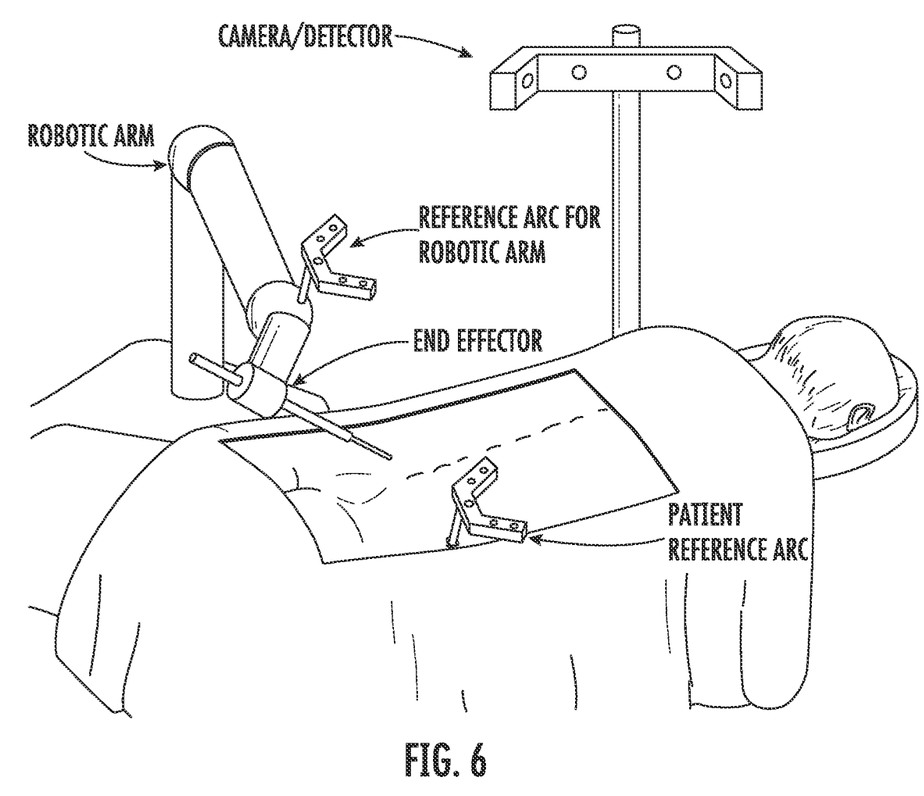
FIG. 6 illustrates at least one embodiment of a robotic system for placing an implant in a spine.
Figure 7A:
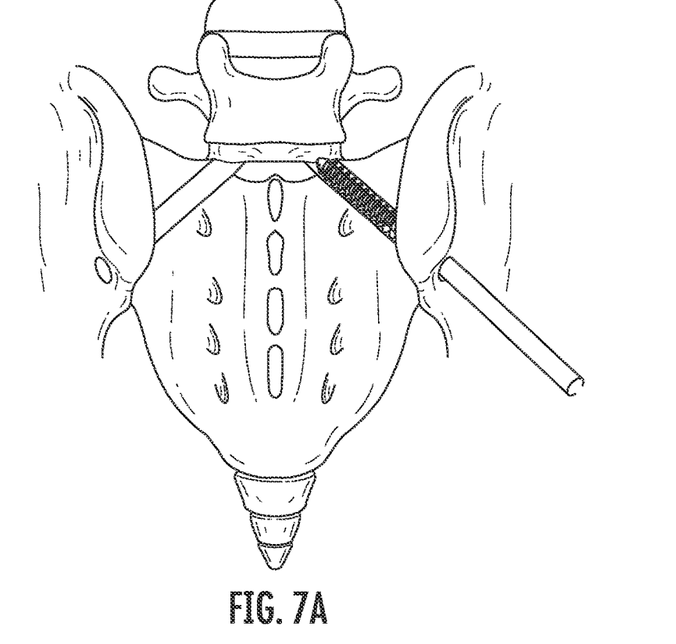
FIG. 7A illustrates a front profile of pathways drilled by an end-effector and created to provide access to the L5/S1 disc space.
Figure 7B:
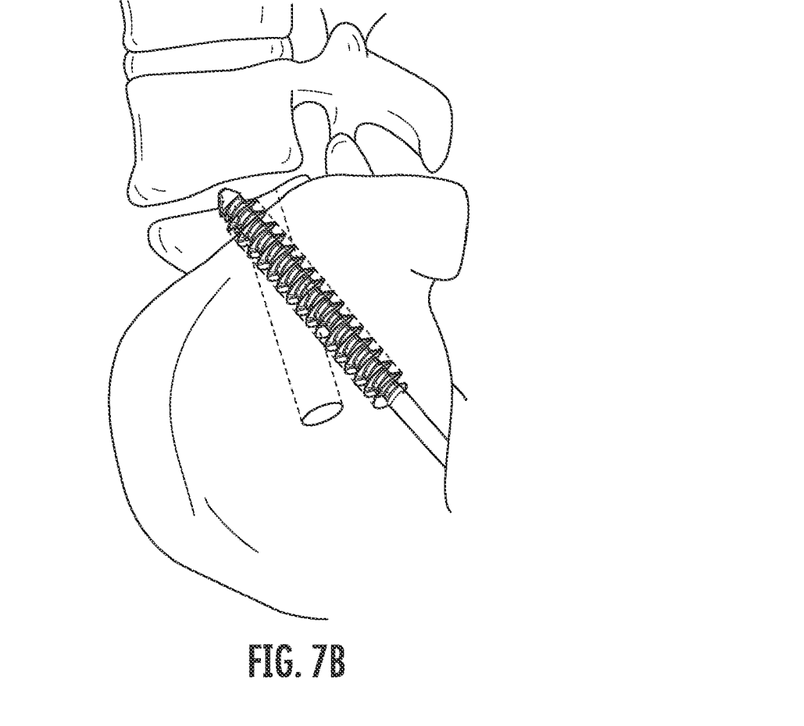
FIG. 7B illustrates a side profile of pathways drilled by an end-effector and created to provide access to the L5/S1 disc space.
Figure 8A:
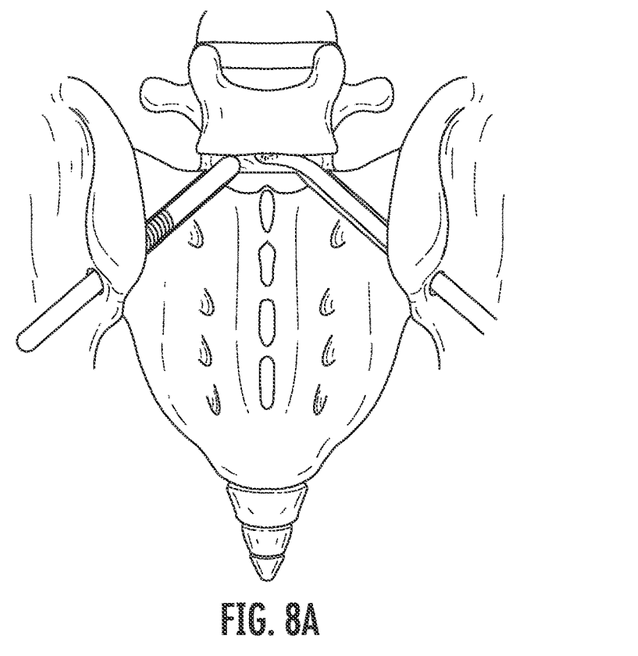
FIG. 8A illustrates a front profile of distraction and disc space preparation in the L5/S1 disc space.
Figure 8B:
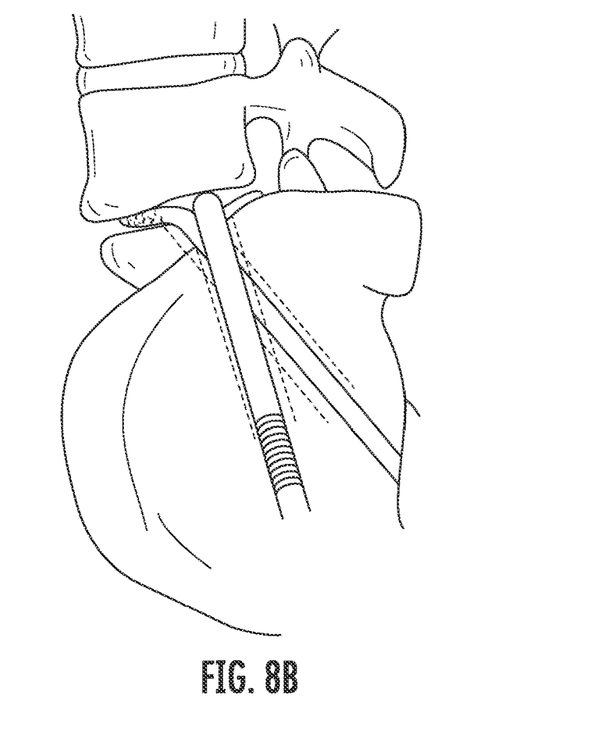
FIG. 8B illustrates a side profile of distraction and disc space preparation in the L5/S1 disc space.
Figure 9A:
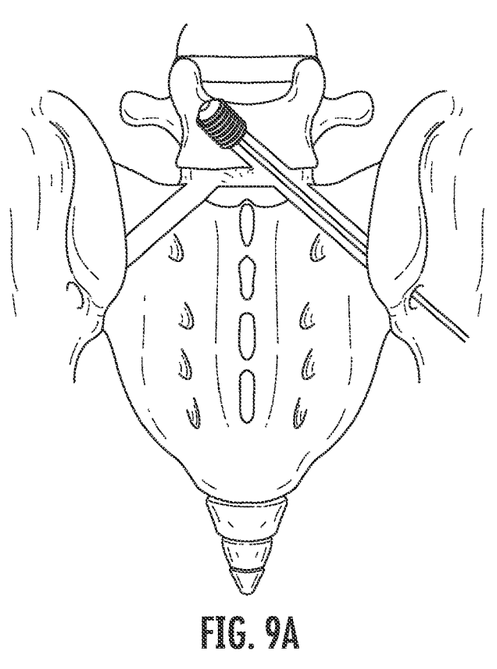
FIG. 9A illustrates a front profile of placement of distal fixation point of the primary fixator implant in the L5/S1 disc space.
Figure 9B:
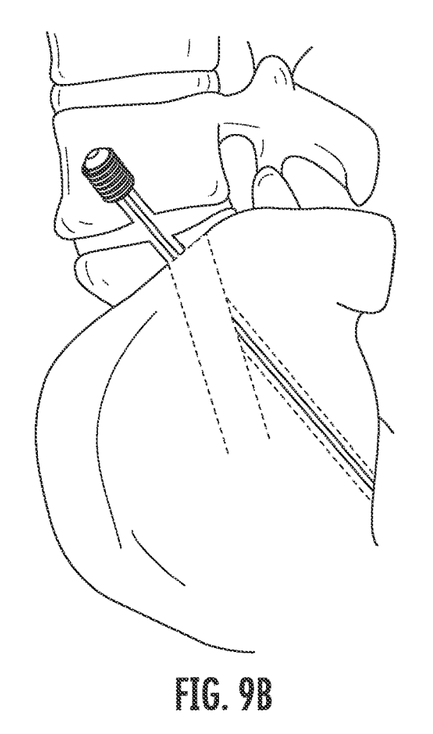
FIG. 9B illustrates a side profile of placement of distal fixation point of the primary fixator implant in the L5/S1 disc space.
Figure 10A:
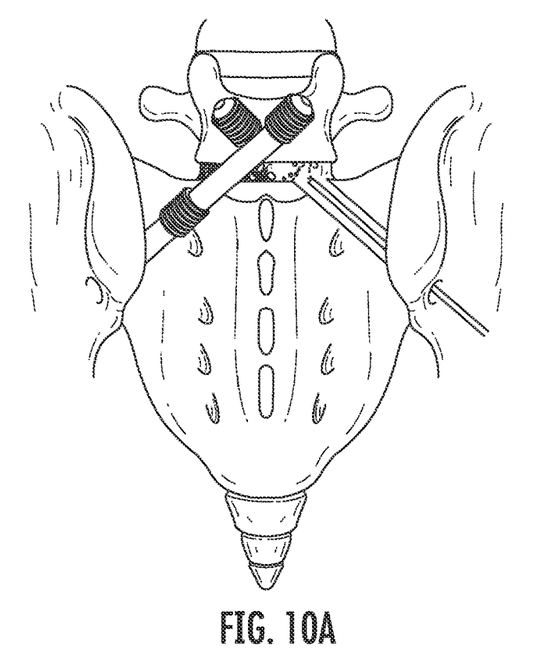
FIG. 10A illustrates a front profile of placement of the secondary fixator implant and impacting bone graft in the L5/S1 disc space.
Figure 10B:
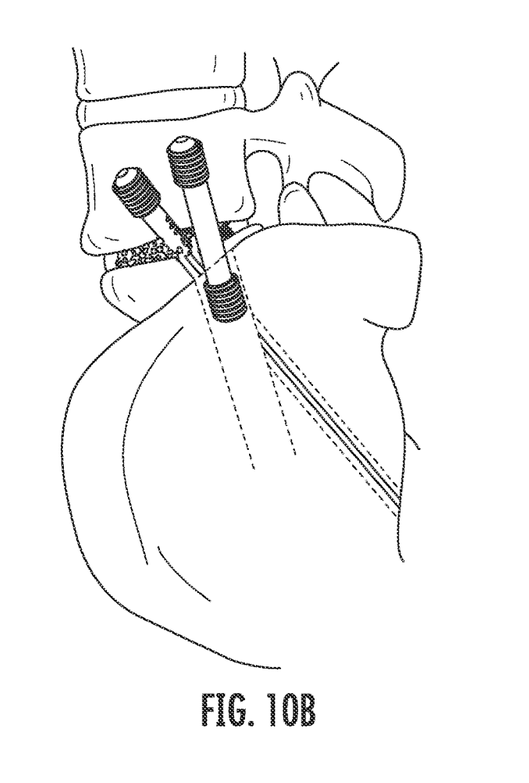
FIG. 10B illustrates a side profile of placement of posterior screw implant and impacting bone graft in the L5/S1 disc space.
Figure 11A:
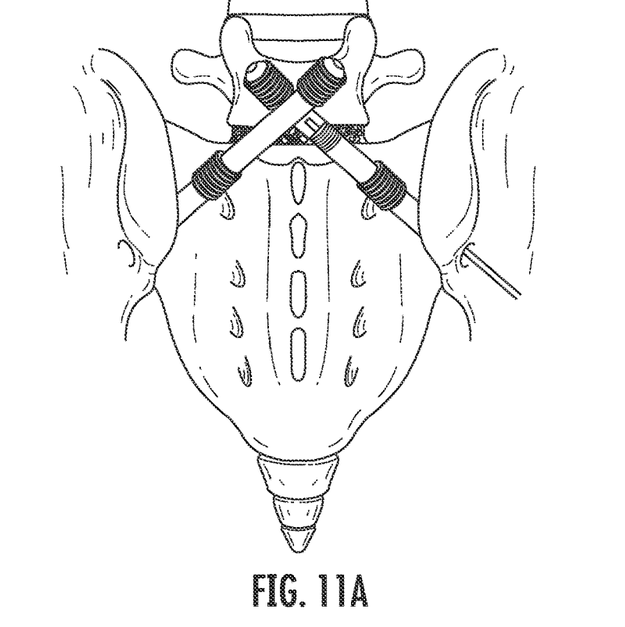
FIG. 11A illustrates a front profile of final assembly of primary and secondary fixator implants in the L5/S1 disc space.
Figure 11B:
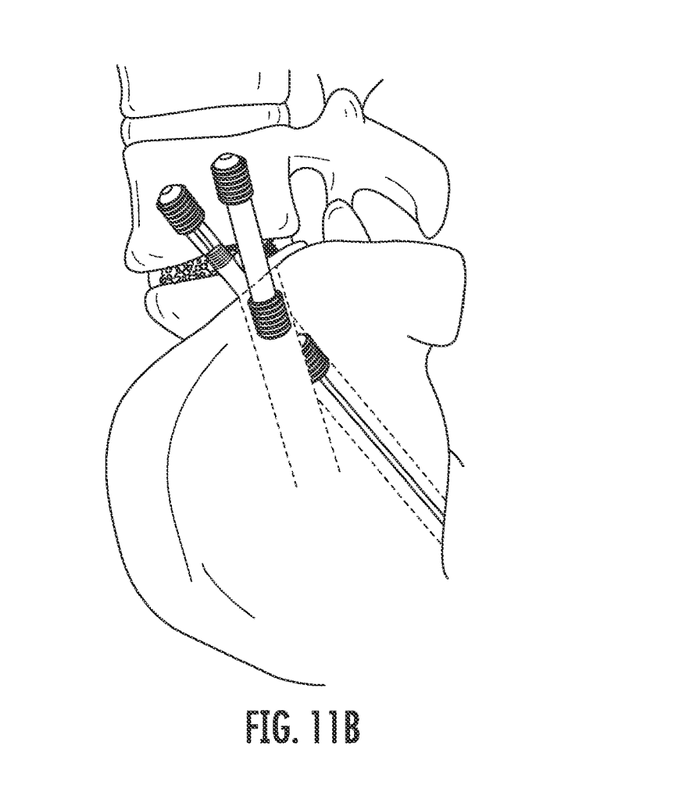
FIG. 11B illustrates a side profile of final assembly of primary and secondary fixator implants in the L5/S1 disc space.
Figure 12A:
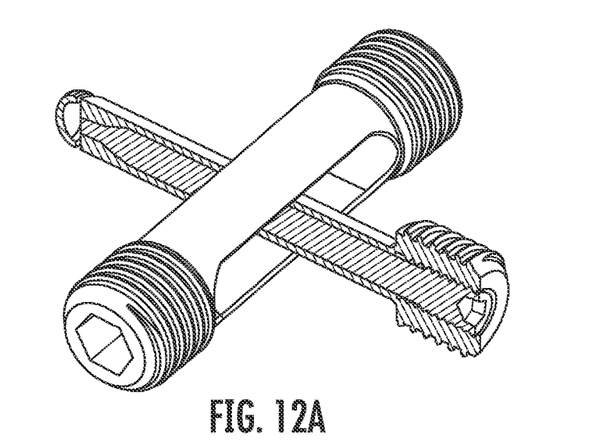
FIG. 12A illustrates a perspective and cross-section view of the primary fixator implant interlocked with secondary fixator implant.
Figure 12B:
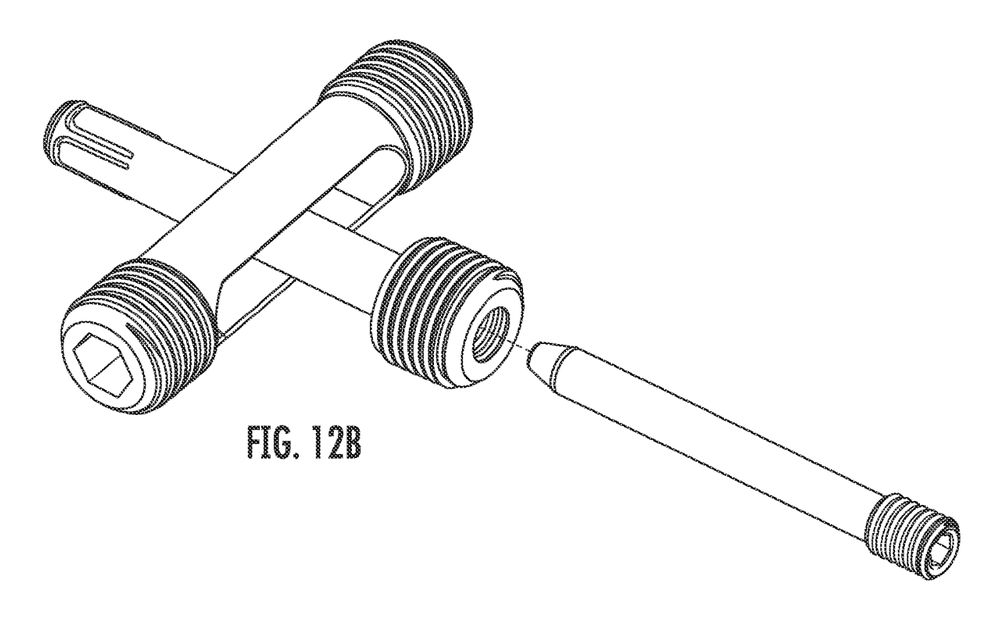
FIG. 12B illustrates a perspective view of the primary fixator implant interlocked with secondary fixator implant with the expansion member poised to enter the secondary fixator.
Figure 13A:
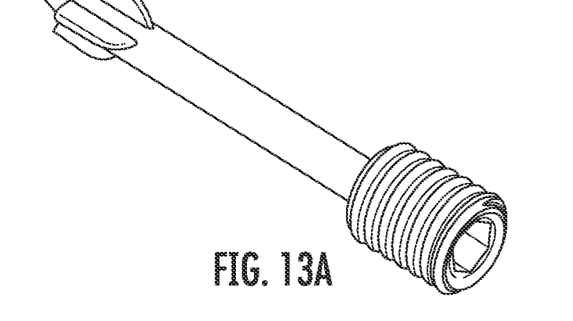
FIG. 13A illustrates a perspective view of the secondary fixator implant with fixation means in an expanded state (i.e. deployed).
Figure 13B:
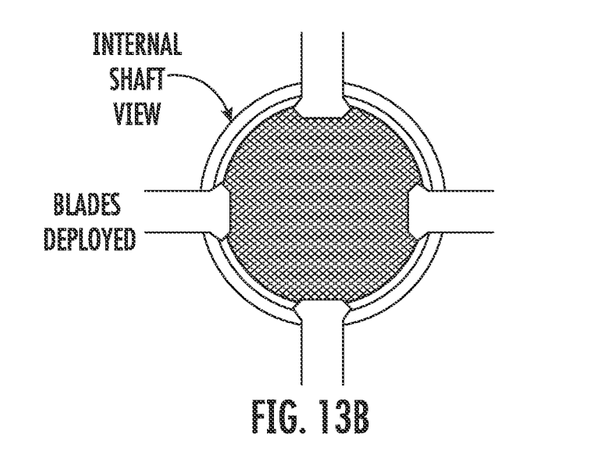
FIG. 13B illustrates a cutaway view of the secondary fixator illustrating the internals of the secondary fixator means with the fixation means expanded.
Figure 13C:
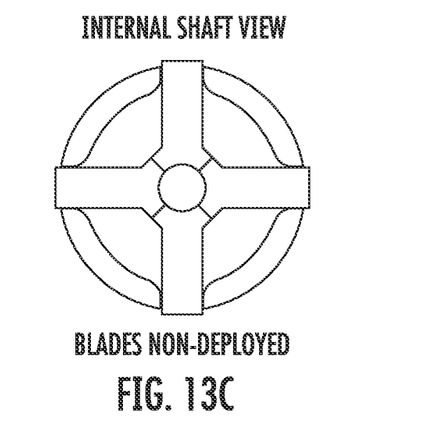
FIG. 13C illustrates a cutaway view of the secondary fixator illustrating the internals of the secondary fixation means with the fixation means retracted internal to the secondary fixation means.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above described embodiments that would still be covered by the present invention.

DETAILED DESCRIPTION OF INVENTION

This disclosure describes the medical method for performing spinal surgical procedures in which a robot controls an instrument that creates a pathway to the spine through one or more ala of a human by a user.

The present invention provides for an improved method for performing spinal Surgical procedures (e.g., spinal fusions) using one or more ala as the pathway to the L5 vertebrae and L5/S1 disc space without violating the sacro-iliac joint. It should be appreciated that on each side of the body there is a continuous bony corridor from the pelvis, through the sacrum, across the L5/S1 disc, and into the L5 vertebral body. Without being bound to any particular theory, these corridors can be traversed by a tunnel that would not damage or endanger any sensitive visceral or neurologic structures. The tunnels could be accessed by percutaneous incisions in the gluteal area.

The present method includes methods and techniques for positioning a patient requiring surgery in a configuration to restrict movement. Upon placement, the patient is monitored for movement in relation to one or more locations of the patients' spine. Three-dimensional (3D) imaging techniques are then used to determine the absolute position of the patients' spine and spinal features of interest to be used in conjunction with the patients' monitored movement, to allow for absolute location, in real time, of a patents spine and its features. The 3D imaging data is processed to determine the optimal pathway to the particular spinal location needing surgery for the specific patient. Using the 3D imaging data, as well as the real-time monitoring information, an end-effector of a robot is used to guide a surgical instrument to the spinal location needing surgery, adjusting its pathway, in real-time, based on a patients' movement relative to the 3D imaging data. Upon creation of the pathway, the desired spinal implant is inserted into the patient. As a result of the aforementioned, the patient obtains the benefit of a spinal fusion without the potential harm created by an extensive surgical approach.

Certain embodiments include additional steps and processes for determining spinal stiffness as well as selecting appropriate implants based on stiffness information.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an', and "the" include singular and plural referents unless the content clearly dictates otherwise. Thus, for example, reference to "a linker" includes one or more linkers.

Unless defined otherwise, all technical and scientific terms used herein have the same meaning as commonly understood by one of ordinary skill in the art.

The phrase "ala", as used herein, generally refers to the wing-like region of the sacrum in a Subject including, but not limited to, the area of bone extending laterally from the first sacral pedicle to the ilium.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The phrase "end-effector" as used herein generally refers to an actuator or manipulator of a robotic arm that moves, directs, interacts or otherwise operates a surgical tool. In some embodiments, a surgical tool may be attached directly to the end of a mechanical or robotic arm, thus in such embodiments the surgical tool is also an end-effector.

The phrase "sacro-spinous space" as used herein generally refers to the non-articular region dorsal to the sacraliliac joint in a subject including, but not limited to, the area between the ilium and the dorsal sacrum.

The phrase "sacro-iliac joint" as used herein generally refers to the surface formed at the area of contact between the sacrum and the ilium.

Robot Techniques

A type of minimally invasive surgery is provided which currently involves using a robot to access internal cavities, bones and organs within Subjects. Robotic surgery has been used in spinal surgeries, for example, to provide accurate placement of pedicle screw. Robotic surgery provides benefits in that the accuracy in positioning the screw within the pedicle reduces the incidence of bony perforation, and thus provides a reduced risk of nerve injury to the Subject. A further practical consequence and advantage of using robotic spine surgery is that surgeons experience less exposure of ionizing radiation because less or no fluoroscopy is necessary to perform the actual procedure.

With use of robotic techniques, positioning a portion of at least one surgical instrument with an end-effector is advantageous because of the accuracy afforded by the robot. In some embodiments, a method may at least include positioning a portion of at least one surgical instrument with an end-effector in at least one ala to enable all or a portion of a surgical procedure to be performed.

In some embodiments, a method may at least include positioning a portion of at least one surgical instrument with an end-effector through at least one ala and sacro-spinous space to enable all or a portion of a surgical procedure at the L5/S1 disc space to be performed.

In some embodiments, a method may at least include positioning a portion of at least one surgical instrument with an end-effector through at least one ala to enable all or a portion of a surgical procedure at the L5/S1 disc space and the L5 vertebra to be performed.

In some embodiments, a method may at least include positioning a portion of at least one surgical instrument with an end-effector through at least one ala to enable all or a portion of a surgical procedure at the ala, L5/S1 disc space and the L5 vertebra to be performed.

In some embodiments, a method may at least include positioning a portion of at least one surgical instrument with an end-effector through at least one ala to enable all or a portion of a surgical procedure at one or more of the ala, L5/S1 disc space and the L5 vertebra to be performed.

In some embodiments, a method may at least include positioning a portion of at least one surgical instrument with an end-effector through at least one ala to enable all or a portion of a surgical procedure at one or more of the ala, L5/S1 disc space and the L5 vertebra to be performed and a non-robotic method for positioning at least one implant in one or more of the: L5 vertebra, L5/S1 disc space and the sacrum.

In some embodiments, a method may at least include a portion of at least one surgical instrument positioned with an end-effector, a controller for controlling the position of the end-effector and a measurement system with a computer processor for measuring: by the processor, a position of the ala of the patient; determining by the processor a change in the position of the ala; and automatically adjusting, via the robot, the position of the end-effector based at least in part on a change in the position of the ala; and automatically adjusting, via the robot, the position of the end-effector to create a pathway in the ala.

In some embodiments, a method may at least include a portion of at least one surgical instrument positioned with an end-effector, a controller for controlling the position of the end-effector and a measurement system with a computer processor for measuring: by the processor, a position of the ala and L5 vertebra of the patient; determining by the processor a change in the position of the ala and L5 vertebra; and automatically adjusting, via the robot, the position of the end-effector based at least in part on a change in the position of the ala and L5 vertebra; and automatically adjusting, via the robot, the position of the end-effector to create a pathway in the ala and L5 vertebra.

In some embodiments, a method may at least include positioning a portion of at least one surgical instrument with an end-effector so that at least one ala and the L5 vertebra are oriented to enable all or a portion of at least one surgical instrument to be positioned.

In some embodiments, a method may at least include positioning a portion of at least one surgical instrument with an end-effector so that at least one ala and the L5 vertebra are oriented to enable all or a portion of at least one surgical implant to be positioned.

In some embodiments, a method may at least include positioning a portion of at least one surgical instrument with an end-effector so that at least one ala and the L5 vertebra are oriented to enable all or a portion of at least one surgical instrument and surgical implant to be positioned.

In some embodiments, a method may at least include a portion of at least one surgical instrument positioned with an end-effector, a controller for controlling the applied load by the end-effector and a measurement system with a computer processor for measuring: by the processor, a displacement of the end-effector.

In some embodiments, a method may at least include a portion of at least one surgical instrument positioned with an end-effector, a controller for controlling the applied load by the end-effector and a measurement system with a computer processor for measuring: by the processor, a displacement of the end-effector after contacting at least one of the ala and L5 vertebra of the patient.

Position and Imaging of Patient

It should be appreciated that with use of robots, that absolute position of surgical locations allow for optimal use of robotic techniques.

It should be appreciated that even with absolute position information, a patient's position needs to be optimized prior to a surgical procedure in order to minimize a patient's movement. As a non-limiting example, certain patients may be placed in the prone position, the upright position, or the side position depending on a patient's weight, age, ailment, or other factors. These positions would be chosen in order to optimize access to the surgical area, while minimizing movements of the patient during the surgical procedure.

Once a patient's position is optimized, embodiments of the invention include monitoring of the patient, or specific locations of a patient, in order to have absolute positions of certain areas of interest of the patient. This information can be used with three-dimensional (3D) imaging data and be used for robotic surgical precision using the 3D imaging and adjusting for a patient's movement during the surgical process.

Several imaging techniques are known in the art. In some embodiments one or more markers are placed or attached on a patient. These markers can be used to provide absolute location information. The position information may be obtained through RF communications, Bluetooth communication, use of reflected infrared light, use of video, or other methods known in the art. It should be appreciated that it is preferred that the monitoring information be provided in real-time to allow for real-time adjustment of the planned surgical pathway of the robot end-effector.

It should be appreciated that the aforementioned position data is used in conjunction with 3D imaging data. There are several three-dimensional (3D) imaging techniques known in the art. Without being bound to a particular 3D imaging technique, typical clinical imaging techniques include computed tomography (CT), magnetic resonance imaging (MRI), diffuse tensor imaging (DTI), cone beam computerized tomography (CBCT), Micro-computed tomography (MCT), tuned-aperture computer tomography (TACT), as well as other methods used in the art.

Embodiments of the invention include pre-processing the 3D imaging data to determine the optimal pathway to the surgical region of interest. Several processing methods are known in the art, and the methods herein are not intended to limit any processing technique employed in the art now, or in the future.

Embodiments of the invention, with use of monitored position data, and use of 3D imaging and processing, allow for the robotic surgical techniques to adjust optimal surgical pathway, in real-time, based on a patients' movement relative to the 3D imaging data.

Stiffness Determination

In some embodiments, a method may at least include a portion of at least one surgical instrument positioned with an end-effector, a controller for controlling the applied load by the end-effector and a measurement system with a computer processor for measuring, by the processor, a displacement of the end-effector after contacting at least one of the ala and L5 vertebra of the patient then determining by the processor a stiffness of at least one of the ala and L5 vertebra.

In some embodiments, a method may at least include selecting an implant based on stiffness information provided by a processor for a controller that positions and measures displacement of at least one surgical instrument that applies load to at least one of the ala and L5 vertebra of the patient.

EXAMPLES

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Example 1

A patient who is in need of surgical spine intervention is presented. The patient is positioned to allow for the placement of fiducial markers in strategic locations of the spine (e.g. L5 vertebra and Sacrum) to detect motions of the L5 vertebra and sacrum throughout the surgical procedure (in real time). 3D imaging techniques of the patient are then employed to determine the spine locations of the patient (L5 vertebra and sacrum) with reference to the fiducial markers.

One or more image processing techniques is used to process the 3D imaging information to establish the optimal pathway through the ala, disc space and L5 vertebra based on the patients' particular spinal arrangement. Upon establishing the optimal pathway, the pathway is surgically executed with an instrument guided by the end-effector of the robot. The robot receives, in real time, updated information from the fiducial markers (either through RF positioning information, reflected infrared light, or other location technique methods known in the art) to ensure the pathway is made using the optimal pathway relative to the patient's movement. Upon establishing the pathway, a spinal implant is inserted into the pathway (either with the aid of a robot or manually).

Example 2

Example 1 is repeated, except that motions of the L5 vertebra and sacrum are monitored with video imaging of the patient throughout the surgical procedure in real-time to detect motion of the of the L5 vertebra and sacrum.

Example 3

Example 1 is repeated, except that after the pathway is established using the robot, the stiffness of the L5 vertebra and/or ala bone is determined by indenting an instrument with a controlled load and measuring its position change.

Example 4

Example 3 is repeated, except that after the stiffness of the L5 vertebra and/or ala bone is determined, the stiffness information is used to assist with the selection of an implant in order to optimize its ability to function (e.g. transmit load) in the bony environment for that specific patient.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A method for performing a spinal surgical procedure in a human using one or more ala as a pathway to an L5 vertebrae and an L5/S1 disc space, the method comprising:
    positioning a portion of at least one surgical instrument with an end-effector in at least one ala to enable all, or a portion of the surgical procedure, to be performed;
    providing a controller for controlling a position of the end-effector and a measurement system with a computer processor, wherein said controller:
        (a) measures a position of the ala of the patient;
        (b) determines, using the processor, a change in the position of the ala, the L5 vertebra, or combinations thereof; and
        (c) automatically adjusts, via a robot, the position of the end-effector based at least in part on a change in the position of the ala, the L5 vertebra, or combinations thereof;
    creating the pathway with the end-effector.

2. The method of claim 1 wherein said surgical procedure is performed and the instrument with the end-effector is removed from the ala prior to completion of the procedure.

3. The method of claim 1 wherein said surgical procedure is performed at the L5/S1 disc space.

4. The method of claim 1 wherein said surgical procedure is performed at the L5/S1 disc space, and the L5 vertebra.

5. The method of claim 1 wherein said processor of said controller further determines a displacement of the end-effector after contacting at least one of the ala and the L5 vertebra of the patient, and determines a stiffness of at least one of the ala and L5 vertebra.

6. The method of claim 5 further comprising selecting an implant based on stiffness of the ala and the L5 vertebra of the patient.

7. A method for performing a spinal surgical procedure in a human using one or more ala and a sacro-spinous space as a pathway to an L5 vertebrae and L5/S1 disc space, the method comprising:
    positioning a portion of at least one surgical instrument with an end-effector through at least one ala to enable all, or a portion of the surgical procedure, to be performed at one or more of the ala, L5/S1 disc space, and the L5 vertebra;
    providing a controller for controlling a position of the end-effector and a measurement system with a computer processor, wherein said system:
        (a) measures a position of the ala of the patient;
        (b) determines, using the processor, a change in the position of the ala, the L5 vertebra, or combinations thereof; and
        (c) automatically adjusts, via a robot, the position of the end-effector based, at least in part, on a change in the position of the ala, the L5 vertebra, or combinations thereof;
    and creating the pathway with the end-effector.

8. The method of claim 7 wherein said portion of the at least one surgical instrument with the end-effector is positioned so that at least one ala and the L5 vertebra are oriented relative to a patient to enable all, or a portion of at least one surgical implant, to be positioned.

9. The method of claim 7 wherein said portion of the at least one surgical instrument with the end-effector is positioned so that at least one ala and the L5 vertebra are oriented to enable all, or a portion of at least one surgical instrument and surgical implant, to be positioned by the robot.

10. The method of claim 7 wherein said controller further determines a displacement of the end-effector, or a displacement of the end-effector after contacting at least one of the ala and the L5 vertebra of the patient.

11. The method of claim 7 wherein said processor of said controller further determines a displacement of the end-effector after contacting at least one of the ala and the L5 vertebra of the patient, and determines a stiffness of at least one of the ala and the L5 vertebra.

12. The method of claim 11 further comprising selecting an implant based on stiffness of the ala and the L5 vertebra of the patient.

13. A method for performing a spinal surgical procedure using one or more ala as a pathway to a spinal location, the method comprising:
    positioning a patient requiring surgery in a configuration to limit movement during a surgical procedure;
    determining an absolute position of the patient's spine and spinal features of interest;
    processing data to orient actual anatomy in a fixed spatial orientation;
    determining an optimal pathway to the spinal location;
    positioning a portion of at least one surgical instrument with an end-effector in at least one ala to enable all or a portion of the surgical procedure to be performed;
    providing a controller for controlling a position of the end-effector and a measurement system with a computer processor, wherein said controller:
        (a) measures a position of the ala of the patient;
        (b) determines, using the processor, a change in the position of the ala, the L5 vertebra, or combinations thereof; and
        (c) automatically adjusts, via a robot, the position of the end-effector based at least in part on a change in a position of the ala, the L5 vertebra, or combinations thereof, to create a pathway in the ala, the L5 vertebra, or combinations thereof;
    creating the pathway with the end-effector; and
    inserting at least one implant into the spinal location of the patient;
    wherein the spinal location is the L5 vertebrae, L5/S1 disc space, ala, sacrum or combinations thereof.

14. The method of claim 13, wherein the surgical procedure is performed without violating the sacro-iliac joint.

15. The method of claim 13, further comprising prior to inserting the implant, inserting a portion of the at least one surgical instrument with the end-effector into the pathway, contacting at least one of the ala and the L5 vertebra of the patient, and determining through use of the processor the stiffness of at least one of the ala and the L5 vertebra based on a displacement of the end-effector upon contacting said at least one of the ala and the L5 vertebra of the patient.

16. The method of claim 15 further comprising selecting an implant based on stiffness of the ala and the L5 vertebra of the patient.

* * * * *